United States Patent
Enzmann et al.

(10) Patent No.: US 6,255,354 B1
(45) Date of Patent: Jul. 3, 2001

(54) PREPARATION OF A PULMONARY SURFACTANT FOR INSTILLATION AND ORAL APPLICATION

(75) Inventors: Franz Enzmann, Bad Homburg (DE); Burkhard Lachmann, Rotterdam (NL)

(73) Assignee: MSE Pharmazeutika GmbH, Bad Homburg (DE)

( * ) Notice: Subject to any disclaimer, the term of this patent is extended or adjusted under 35 U.S.C. 154(b) by 0 days.

(21) Appl. No.: 09/355,933

(22) PCT Filed: Feb. 11, 1998

(86) PCT No.: PCT/EP98/00745

§ 371 Date: Oct. 12, 1999

§ 102(e) Date: Oct. 12, 1999

(87) PCT Pub. No.: WO98/35661

PCT Pub. Date: Aug. 20, 1998

(30) Foreign Application Priority Data

Feb. 12, 1997 (DE) .............................................. 197 05 230

(51) Int. Cl.$^7$ ............................. A61K 31/12; A61K 35/42
(52) U.S. Cl. ............................................. 514/690; 424/557
(58) Field of Search ............................. 514/690; 424/557

(56) References Cited

U.S. PATENT DOCUMENTS 4,654,373 * 3/1987 Bertelli ................................. 514/690

FOREIGN PATENT DOCUMENTS 2092969   12/1996   (ES) .

* cited by examiner

Primary Examiner—Theodore J. Criares
Assistant Examiner—Jennifer Kim
(74) Attorney, Agent, or Firm—Jacobson Holman PLLC

(57) ABSTRACT

A pulmonary surfactant formulation for instillation and oral application, containing at least 0.1% by weight of 2,3-dimethoxy-5-methyl-6-decaprenyl-1,4-benzoquinone in addition to an effective amount of pulmonary surfactant and usual excipients.

12 Claims, No Drawings

PREPARATION OF A PULMONARY SURFACTANT FOR INSTILLATION AND ORAL APPLICATION

This application is a 371 of PCT/EP98/00745 filed Feb. 11, 1998.

Pulmonary surfactant is a complex of phospholipids, neutral lipids and surfactant proteins which together form a monolayered barrier between the air and the liquid surface of the lung. Pulmonary surfactant is produced in the alveolar type II cells from which it is released into the alveolar space. Pulmonary surfactant can be obtained by extraction or recombination.

To date, pulmonary surfactant has been employed for instillation in diseases or deficiencies of the lung, especially in IRDS, the respiratory distress syndrome in children, and in ARDS.

It has now been found that also for the oral treatment of diseases of the entire digestive tract (mouth, esophagus, stomach and intestine), the effectiveness and the shelf life of pulmonary surfactant can be increased by an addition of at least 0.1% by weight of 2,3-dimethoxy-5-methyl-6-decaprenyl-1,4-benzoquinone.

2,3-Dimethoxy-5-methyl-6-decaprenyl-1,4-benzoquinone is also known by the designation of coenzyme Q10. This substance plays a role in the respiratory chain and, in addition, is an antioxidant which is capable of scavenging free radicals, which are transmitted by vitamins, in particular. In addition, Q10 determines the elasticity and dynamics of cell membranes. Therefore, it has been recommended as a monopreparation and in combination with other active substances for oral administration. Further, it is offered for skin care in the form of a liposome cream which allows the active ingredient to penetrate through the horny layer barriers and then to accumulate in the various strata of the skin. However, this does not provide any indication of that even small amounts of this substance are capable of stabilizing the active substance, pulmonary surfactant, and enhancing its effectiveness. In particular, higher amounts of the active substance 2,3-dimethoxy-5-methyl-6-decaprenyl-1,4-benzoquinone are capable, when instilled into the lung, of strengthening the lung-resident immune system, of helping the cell to regenerate damaged cellular structures, and of simultaneously enhancing the effectiveness of pulmonary surfactant.

It is surprising thet Q10 provides dynamics not only to the lipid bilayers, but also to the pulmonary surfactant system.

Thus, the present invention relates to pulmonary surfactant formulations for instillation containing at least 0.1% by weight of 2,3-dimethoxy-5-methyl-6-decaprenyl-1,4-benzoquinone in addition to an effective amount of pulmonary surfactant and usual excipients.

The amount of 2,3-dimethoxy-5-methyl-6-decaprenyl-1,4-benzoquinone may be increased to a weight ratio of 1:1 with the pulmonary surfactant, whereby special therapeutic effects are achieved.

What is claimed is:

1. A pulmonary surfactant formulation comprising effective amounts of 2,3-dimethoxy-5-methyl-6-decaprenyl-1,4-benzoquinone and pulmonary surfactant.

2. A formulation of claim 1, wherein effective amounts of 2,3-dimethoxy-5-methyl-6-decaprenyl-1,4-benzoquinone and pulmonary surfactant are in the weight ratio from 0.1:1 to 1:1.

3. A formulation of claim 2, in a form to be administered orally.

4. A formulation of claim 2, suitable for instillation.

5. A formulation of claim 1, in a form to be administered orally.

6. A formulation of claim 1, suitable for instillation.

7. A formulation of claim 1, further comprising excipients.

8. A formulation of claim 2, further comprising excipients.

9. A formulation of claim 3, further comprising excipients.

10. A formulation of claim 4, further comprising excipients.

11. A formulation of claim 5, further comprising excipients.

12. A formulation of claim 6, further comprising excipients.

* * * * *